United States Patent
Irby et al.

[11] Patent Number: 5,938,304
[45] Date of Patent: Aug. 17, 1999

[54] PROTECTIVE COVER ARRANGEMENT FOR DIALYSIS MACHINES

[76] Inventors: John M. Irby; Bridgette Brown, both of 25771 Wolfcreek Rd., Pass Christian, Miss. 39571

[21] Appl. No.: 09/135,457

[22] Filed: Aug. 17, 1998

[51] Int. Cl.[6] ................................... A47B 77/06
[52] U.S. Cl. .............................. 312/229; 312/209
[58] Field of Search ................. 312/229, 257.1, 312/209, 140.1, 140.3, 211, 228

[56] References Cited

U.S. PATENT DOCUMENTS

| | | | |
|---|---|---|---|
| 477,758 | 6/1892 | Huss | 312/229 |
| 1,088,783 | 3/1914 | Lisbae | 312/229 X |
| 2,614,401 | 10/1952 | Roberts | 62/258 |
| 3,085,842 | 4/1963 | Johnson | 312/209 |
| 3,333,913 | 8/1967 | Heisler | 312/244 |
| 3,606,508 | 9/1971 | Burnes | 312/140.3 |
| 3,789,823 | 2/1974 | Doskocil | 126/42 |
| 3,868,154 | 2/1975 | MacDonald et al. | 312/209 |
| 3,949,902 | 4/1976 | Thompson | 312/229 X |
| 4,230,381 | 10/1980 | Rhoades | 312/295 |
| 5,294,194 | 3/1994 | Lombardo | 312/229 |
| 5,613,747 | 3/1997 | Becker et al. | 312/228 X |
| 5,695,262 | 12/1997 | Wachtler | 312/209 X |

FOREIGN PATENT DOCUMENTS

| | | | |
|---|---|---|---|
| 759665 | 5/1967 | Canada | 312/229 |

*Primary Examiner*—Peter M. Cuomo
*Assistant Examiner*—James O. Hansen
*Attorney, Agent, or Firm*—Henderson & Sturm

[57] ABSTRACT

A protective cover arrangement 10 for the lower portion 101 of the front face 102 and base portion 103 of a dialysis machine 100. The arrangement 10 includes a bottom cover unit 12 that includes a generally rectangular horizontal framework member 30 having a shallow collection receptacle 31 that covers the front end of the base portion 103 of the dialysis machine 100, and a raised wall panel 35 that is overlapped by the upper portion 104 of the front face 102 of the dialysis machine 100, a liquid collection reservoir 33 disposed on the back end of the base portion 103 of the dialysis machine 100, and at least one gutter 32 operatively associated with one side of the dialysis machine 100, wherein the at least one gutter 32 establishes fluid communication between the receptacle 31 and the reservoir 33.

3 Claims, 1 Drawing Sheet

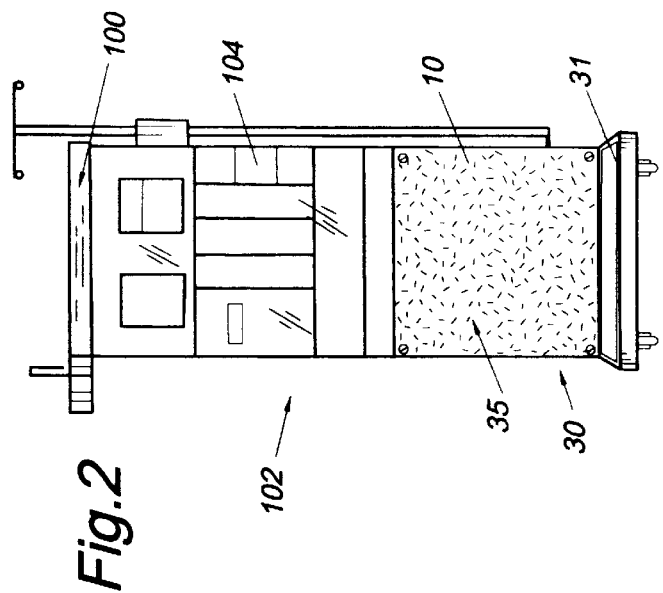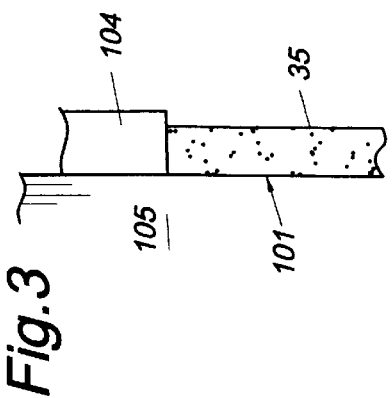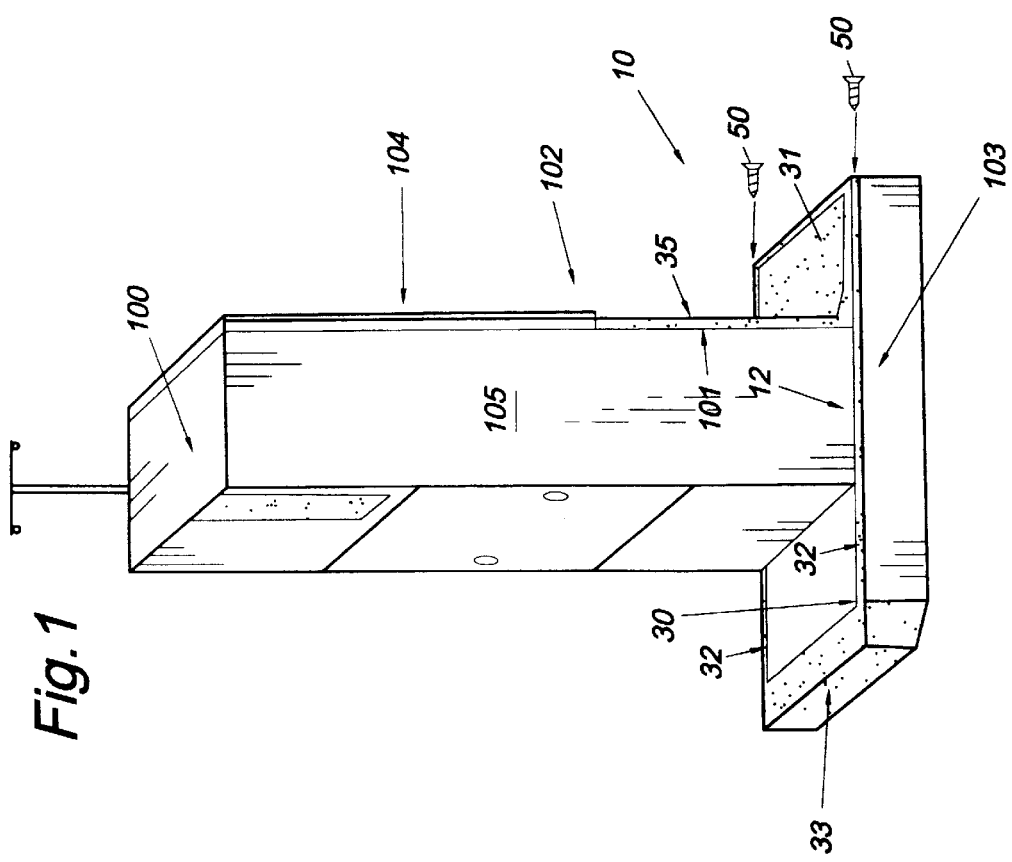

PROTECTIVE COVER ARRANGEMENT FOR DIALYSIS MACHINES

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of protective covers in general, and in particular to a protective cover arrangement for selective portions of a dialysis machine.

2. Description of Related Art

As can be seen by reference to the following U.S. Pat. Nos. 2,614,401; 3,333,913; 3,789,823; and 4,230,381, the prior art is replete with myriad and diverse protective cover devices.

While all of the aforementioned prior art constructions are more than adequate for the basic purpose and function for which they have been specifically designed, they are uniformly deficient with respect to their failure to provide a simple, efficient, and practical multi-component protective cover for the top, front, and base portions of a conventional dialysis machine.

As most health care professionals are all too well aware, a patient's perception of the quality and condition of medical equipment has a definite bearing on the patient's comfort level regarding the medical treatment that they are undergoing, and the more modern and well maintained the medical equipment appears, the lower the stress levels experienced by the patient.

As a consequence of the foregoing situation, there has existed a longstanding need for a new and improved protective cover arrangement specifically designed for the lower, portion of a dialysis machine to maintain that surface in pristine condition, and the provision of such a construction is a stated objective of the present invention.

BRIEF SUMMARY OF THE INVENTION

Briefly stated, the protective cover arrangement that forms the basis of the present invention comprises in general, a base cover unit, which provides a protective cover over the base portion of a conventional dialysis machine.

As will be explained in greater detail further on in the specification, the bottom cover unit is provided with a shallow liquid collection receptacle that covers the front end of the base portion of the dialysis machine, and rear end of the receptacle is provided with a raised wall that is overlapped by the bottom of the face panel of the dialysis machine.

In addition, the shallow liquid collection receptacle is operatively connected to a liquid collection reservoir via a gutter arrangement such that liquid will drain from the receptacle to the reservoir. The overall effect of the protective cover arrangement will be to maintain a clean and modern appearance to the top, front face, and base portion of the dialysis machine.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the protective cover arrangement deployed on a dialysis machine;

FIG. 2 is a front view of the protective cover arrangement; and

FIG. 3 is an isolated detail view of the operative cooperation between the upper portion of the front face of the dialysis machine and a portion of the base cover unit.

DETAILED DESCRIPTION OF THE INVENTION

As can be seen by reference to the drawings, and in particularly to FIG. 1, the protective cover arrangement that forms the basis of the present invention is designated generally by the reference number 10. The cover arrangement 10 comprises in general, a base cover unit 12.

As shown in FIG. 1, the cover arrangement 10 is intended to cover the lower portion 101 of the front face 102, and base portion 103 of a conventional dialysis machine 100, having a generally inverted T-shaped configuration, wherein the upper portion 104 of the front face 102 of the dialysis machine 100 projects slightly beyond the lower portion 101. The stem of the inverted T-shaped configuration comprises the generally elongated rectangular dialysis machine housing 105 and the cross arms of the inverted T-shaped configuration comprises the base portion 103 of the dialysis machine 100.

As shown in FIGS. 1 through 3, the base cover unit 12 comprises a generally rectangular, horizontal framework member 30 preferably fabricated from stainless steel or the like. The front portion of the framework member 30 defines a shallow liquid collection receptacle 31, the sides of the framework member 30 define gutters 32, and the rear portion of the framework member 30 define a liquid collection reservoir 33.

In addition, the shallow liquid collection receptacle 31 at the front of the dialysis machine 100 is provided with a raised transparent wall panel 35 which covers the lower portion 101 of the front face 102 of the dialysis machine. The top edge of the wall panel 35 is dimensioned to be recessed from the bottom of the upper portion 104 of the front face 102 of the dialysis machine 100 which will form a slight overhang relative to the vertical wall panel 35 on the generally rectangular horizontal framework member 30. Any liquid splashed and/or spilled on the upper portion 104 of the front face 102 of the dialysis machine 100 will fall by gravity onto the wall panel 35 of the framework member 30 and be collected in the liquid collection receptacle 31. Thereafter, the liquid in the collection receptacle 31 will travel via the side gutters 32 into the liquid collection reservoir 33 at the rear of the base portion 103 of the dialysis machine 100 to be disposed of when the machine 100 is not in use. In addition, the wall panel 35 of the framework member 30 may be secured to the front face 102 of the dialysis machine via conventional fasteners 50.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

We claim:

1. A protective cover arrangement in combination with a generally inverted T-shaped dialysis machine having a front face divided into an upper portion having a bottom which slightly overhangs a lower portion, and a base portion having a front end and a rear end wherein the cover arrangement comprises:

a bottom cover unit including generally rectangular horizontal framework member having a shallow collection receptacle having a front end and a rear end and dimensioned to cover the front end of the base portion of the dialysis machine, a vertical wall panel projecting upwardly from the rear end of the shallow collection receptacle, a liquid collection reservoir disposed on the rear end of the base portion of the dialysis machine, a pair of gutters disposed along both sides of the dialysis machine and extending from said receptacle to said reservoir.

2. The cover arrangement as in claim 1 wherein the vertical wall panel is adapted to be secured to the lower portion of the front face of the dialysis machine.

3. The cover arrangement as in claim 2 wherein the vertical wall panel is dimensioned to be recessed relative to the bottom of the upper portion of the front face of the dialysis machine.

* * * * *